United States Patent [19]

Okushima et al.

[11] Patent Number: 5,246,958
[45] Date of Patent: Sep. 21, 1993

[54] ANTIHYPERTENSIVE THIOCARBAMOYLASCETONITRILE COMPOUNDS

[75] Inventors: Hiromi Okushima, Kawasaki; Akihiro Tobe, Yokohama; Makio Kobayashi, Machida; Tetsuro Shimpuku, Setagaya; Hideki Bessho, Zama; Junko Hayashi, Itabashi; Asami Seino, Yokohama, all of Japan

[73] Assignee: Mitsubishi Kasei Corporation, Tokyo, Japan

[21] Appl. No.: 664,053

[22] Filed: Mar. 4, 1991

[30] Foreign Application Priority Data

Mar. 5, 1990 [JP] Japan .................. 2-53309

[51] Int. Cl.$^5$ .............. C07C 327/44; C07D 233/64; C07D 333/24; A61K 31/275
[52] U.S. Cl. .............................. 514/399; 548/336.1; 548/338.5; 548/339.5; 548/341.5; 548/343.1; 548/343.5; 548/180; 548/309.7; 544/334; 544/335; 544/358; 546/149; 546/176; 546/330; 558/388; 558/389; 558/392
[58] Field of Search ............... 548/346, 343.5, 336.1, 548/338.5, 343.1, 331.5; 514/399

[56] References Cited

U.S. PATENT DOCUMENTS

| | | | |
|---|---|---|---|
| 4,379,154 | 4/1983 | Aloup et al. | 424/250 |
| 4,456,758 | 6/1984 | Aloup et al. | 546/284 |
| 4,466,866 | 8/1984 | Bizot et al. | 204/78 |
| 4,568,682 | 2/1986 | Aloup et al. | 514/336 |
| 4,751,234 | 6/1988 | Aloup et al. | 514/314 |

FOREIGN PATENT DOCUMENTS

| | | |
|---|---|---|
| 0257882 | 3/1988 | European Pat. Off. |
| 0321273 | 6/1989 | European Pat. Off. |
| 0321274 | 6/1989 | European Pat. Off. |
| 0326297 | 8/1989 | European Pat. Off. |
| 122087 | 9/1976 | Fed. Rep. of Germany |

OTHER PUBLICATIONS

Pesson et al., *C.R. Acad. Sci., Paris, Ser. C,* 266(21) pp. 1555–1558 (1968).

Chemical Abstracts, vol. 77 (19), entry 126186y (1972).
B. Milczarska, et al., Chemical Abstract, vol. 96, No. 1 (293e), p. 23, (1982).
M. Augustin, et al., Chemical Abstract, vol. 97, No. 11, (92199a), pp. 763, 764, (1982).

*Primary Examiner*—Floyd D. Higel
*Attorney, Agent, or Firm*—David G. Conlin; Ernest V. Linek

[57] ABSTRACT

Disclosed are antihypertensive pharmaceutical compositions and compounds which include the thiocarbamoylacetonitrile having the formula:

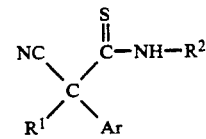

wherein:

$R^1$ is selected from the group consisting of hydrogen, a $C_1$ to $C_6$ alkyl, a $C_3$ to $C_6$ cycloalkyl or —(CH$_2$)$_n$—A (where A is selected from the group consisting of a $C_6$ to $C_{12}$ aryl, a 5- or 6-membered heterocyclic group or a fused heterocyclic group constituted by 9 or 10 atoms, each of which may be substituted by at least one substitute group selected from a $C_1$ to $C_6$ alkyl and a halogen and n is 0 or an integer of 1 to 6), $R^2$ represents a $C_1$ to $C_{10}$ alkyl, and Ar represents an aryl, a 5- or 6-membered heterocyclic group or a fused heterocyclic group, each of which may be substituted by at least one substituent group selected from the group consisting of a $C_1$ to $C_6$ alkyl, a $C_1$ to $C_6$ alkoxy, a $C_2$ to $C_7$ alkylcarbonyl, a $C_7$ to $C_6$ dialkylamino, amino, formylamino, a $C_2$ to $C_7$ alkylcarbonylamino, a halogen, cyano, nitro, hydroxyl, a $C_1$ to $C_6$ alkylthio, a $C_6$ to $C_{12}$ arylsulfinyl, a $C_1$ to $C_6$ alkylsulfinyl, a $C_6$ to $C_{12}$ alkylsulfonyl, a $C_6$ to $C_{12}$ arylsulfonyl, aminosulfonyl, a $C_1$ to $C_6$ alkylaminosulfonyl, a $C_2$ to $C_6$ dialkylaminosulfonyl, trifluoromethyl and imidazolyl.

8 Claims, No Drawings

ANTIHYPERTENSIVE THIOCARBAMOYLASCETONITRILE COMPOUNDS

BACKGROUND OF THE INVENTION

This invention relates to novel thiocarbamoylacetonitrile derivatives and pharmaceutical compositions containing the same, and having antihypertensive activity.

There have previously been proposed various compounds having antihypertensive activity. For example, it is known that a thioformamide derivative having a heterocyclic group such as pyridine or quinoline is capable of lowering the pressure of artery the "spontaneous hypertension rat" (or SHR) (see Japanese Provisional Patent Publications No. 42687/1982, No. 38281/1983, No 7188/1984 and No. 232281/1984).

However, the above-reference thioformamide compound, which can be practically applied as an antihypertensive agent, is not necessarily sufficient and it is thus necessary to develop other antihypertensive agents, having greater effective activity.

SUMMARY OF THE INVENTION

The present inventors have intensively studied this situation with the goal of providing a novel compound having good antihypertensive activity and, they have found that by using a thiocarbamoylacetonitrile derivative in which a specific aryl group is replaced at the α-position of the acetonitrile, the above-stated objective (i.e., increased antihypertensive activity).

The antihypertensive, a thiocarbamoylacetonitrile derivative of the present invention comprises a compound represented by the following formula:

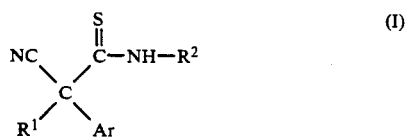

(I)

wherein:

$R^1$ is selected from the group consisting of hydrogen, a $C_1$ to $C_6$ alkyl, a $C_3$ to $C_6$ cycloalkyl or $-(CH_2)_n-A$ (where A represents a $C_6$ to $C_{12}$ aryl, a 5- or 6-membered heterocyclic group or a fused heterocyclic group of by 9 or 10 atoms, each of which may be substituted by at least one member selected from the group consisting of a $C_1$ to $C_6$ alkyl and a halogen, and n is 0 or a positive integer of 1 to 6), $R^2$ represents a $C_1$ to $C_{10}$ alkyl, and Ar represents an aryl, a 5- or 6-membered heterocyclic group or a fused heterocyclic group, each of which may be substituted by at least one substituent selected from the group consisting of a $C_1$ to $C_6$ alkyl, a $C_1$ to $C_6$ alkoxy, a $C_2$ to $C_7$ alkylcarbonyl, a $C_7$ to $C_{13}$ arylcarbonyl, a $C_1$ to $C_6$ alkylamino, a $C_2$ to $C_6$ dialkylamino, amino, formylamino, a $C_2$ to $C_7$ alkylcarbonylamino, a halogen, cyano, nitro, hydroxyl, a $C_1$ to $C_6$ alkylthio, a $C_6$ to $C_{12}$ arylthio, a $C_1$ to $C_6$ alkylsulfinyl, a $C_6$ to $C_{12}$ arylsulfinyl, a $C_1$ to $C_6$ alkylsulfonyl, a $C_6$ to $C_{12}$ arylsulfonyl, aminosulfonyl, a $C_1$ to $C_6$ alkylaminosulfonyl, a $C_2$ to $C_6$ dialkylaminosulfonyl, trifluoromethyl and imidazolyl.

DESCRIPTION OF THE PREFERRED EMBODIMENTS

As set forth above, the antihypertensive thiocarbamoylacetonitrile derivative of the present invention is represented by the above formula (I).

In the above formulae, $R^1$ represents hydrogen; $C_1$ to $C_6$-straight or branched alkyl such as methyl, ethyl, n-propyl, isopropyl, n-butyl, tert-butyl, n-pentyl and n-hexyl; $C_3$ to $C_6$-cycloalkyl such as cyclopropyl, cyclobutyl, cyclopentyl and cyclohexyl; or $-(CH_2)_n-A$ (each A represents $C_6$ to $C_{12}$ aryl such as phenyl and naphthyl; a 5- or 6-membered heterocyclic group such as pyrrolyl, imidazolyl, pyrazolyl, pyridyl, pyradinyl, pyrimidinyl, pyridazinyl, thienyl, thiazolyl, isothiazolyl, furyl, oxazolyl and isoxazolyl; or a fused heterocyclic group constituted by 9 to 10 atoms such as indolydinyl, indolyl, isoindolyl, quinolyl, isoquinolyl, benzothienyl, isobenzothienyl, benzothiazolyl, isobenzothiazolyl, benzofuranyl, isobenzofuranyl, benzoxazolyl, isobenzoxazolyl and benzimidazolyl; each of which may be substituted by at least one substituent selected from a halogen such as fluorine, chlorine and bromine; and a lower alkyl such as methyl, ethyl, n-propyl, isopropyl, n-butyl, tert-butyl, n-pentyl and n-hexyl; and n represents 0 or a positive integer of 1 to 6,);

$R^2$ represents $C_1$ to $C_{10}$ alkyl such as methyl, ethyl, n propyl, isopropyl, n-butyl, n-pentyl, n-hexyl, n-heptyl, n-heptyl, n-octyl, n-nonyl and n-decyl;

Ar represents a $C_6$ to $C_{12}$ aryl such as phenyl, tolyl, xylyl and naphthyl; a 5- or 6-membered heterocyclic group such as pyrrolyl, imidazolyl, pyrazolyl, pyridyl, pyrazinyl, pyrimidinyl, pyridazinyl, thienyl, thiazolyl, isothiazolyl, furyl, oxazolyl and isoxazolyl; or a fused heterocyclic group constituted by 9 to 10 atoms such as indolydinyl, indolyl, isoindolyl, quinolyl, isoquinolyl, benzothienyl, isobenzothienyl, benzothiazolyl, isobenzothiazolyl, benzofuranyl, isobenzofuranyl, benzoxazolyl, isobenzoxazolyl and benzimidazolyl; each of which may be substituted by at least one selected from a $C_1$ to $C_6$ alkyl such as methyl, ethyl, n-propyl, isopropyl, n-butyl, tertbutyl, n-pentyl and n-hexyl; a $C_1$ to $C_6$ alkoxy such as methoxy, ethoxy, n-propoxy, isopropoxy, n-butoxy, tertbutoxy, n-pentyloxy and n-hexyloxy; a $C_2$ to $C_7$ alkylcarbonyl such as acetyl, propionyl, butyryl, isobutyryl, valeryl, isovaleryl and pivaloyl; a $C_7$ to $C_{13}$ arylcarbonyl such as benzoyl and naphthoyl; a $C_1$ to $C_6$ alkylamino such as methylamino, ethylamino, n-propylamino, isopropylamino and n-butylamino; a $C_2$ to $C_6$ dialkylamino such as dimethylamino, diethylamino and methylethylamino; amino; formyl; a $C_2$ to $C_7$ alkylcarbonylamino such as acetylamino, propionylamino and butyrylamino; a halogen such as fluorine, chlorine and bromine; cyano; nitro; hydroxyl; a $C_1$ to $C_6$ alkylthio such as methylthio, ethylthio, n-propylthio, isopropylthio, n-butylthio, tertbutylthio, n-pentylthio and n-hexylthio; an arylthio such as phenylthio and naphthylthio; a $C_1$ to $C_6$ alkylsulfinyl such as methylsulfinyl, ethylsulfinyl, n-propylsulfinyl, isopropylsulfinyl, n-butylsulfinyl, tert-butylsulfinyl, n-pentylsulfinyl and n-hexylsulfinyl; a $C_6$ to $C_{12}$ arylsulfinyl such as phenylsulfinyl and naphthylsulfinyl; a $C_1$ to $C_6$ alkylsulfonyl such as methylsulfonyl, ethylsulfonyl, n-propylsulfonyl, isopropylsulfonyl, n-butylsulfonyl, tert-butylsulfonyl, n-pentylsulfonyl and n-hexylsulfonyl; a $C_6$ to $C_{12}$ arylsulfonyl such as phenylsulfonyl and naphthylsulfonyl; aminosulfonyl; a $C_1$ to $C_6$ alkylaminosulfonyl such as methylaminosulfonyl, ethylaminosulfonyl, n-propylaminosulfonyl, isopropylaminosulfonyl, n-butylaminosulfonyl, tert-butylaminosulfonyl, n-pentylaminosulfonyl and n-hexylaminosulfonyl; a $C_2$ to $C_6$ dialkylaminosulfonyl such as dimethylaminosulfonyl and diethylaminosulfonyl; trifluoromethyl and imidazolyl.

In the present invention, preferred compounds include those wherein $R^1$ represents hydrogen, the aforesaid $C_1$ to $C_6$ alkyl, a $C_3$ to $C_6$ cycloalkyl or —(CH$_2$)$_n$—A (where A represents a phenyl, pyridyl, thienyl, benzimidazolyl or benzothiaolyl, each of which may be substituted by at least one selected from a $C_1$ to $C_3$ alkyl and a halogen, and n is 0 or a positive integer of 1 to 3), $R^2$ represents the aforesaid $C_1$ to $C_6$ alkyl, and Ar represents phenyl, naphthyl, pyridyl, thienyl, pyrrolyl, imidazolyl, pyradinyl, pyrimidinyl, indolyl, benzothiazolyl, benzimidazolyl or quinolyl, each of which may be substituted by at least one substituent selected from the group consisting of a $C_1$ to $C_6$ alkyl, a $C_1$ to $C_6$ alkoxy, a $C_2$ to $C_7$ alkylcarbonyl, a $C_7$ to $C_{13}$ arylcarbonyl, a $C_1$ to $C_6$ alkylamino, a $C_2$ to $C_6$ dialkylamino, amino, formylamino, a $C_2$ to $C_7$ alkylcarbonylamino, a halogen, cyano, nitro, hydroxyl, a $C_1$ to $C_6$ alkylthio, a $C_6$ to $C_{12}$ arylthio, a $C_1$ to $C_6$ alkylsulfinyl, a $C_6$ to $C_{12}$ arylsulfinyl, a $C_1$ to $C_6$ alkylsulfonyl, a $C_6$ to $C_{12}$ arylsulfonyl, aminosulfonyl, a $C_1$ to $C_6$ alkylaminosulfonyl, a $C_2$ to $C_6$ dialkylaminosulfonyl, trifluoromethyl and imidazolyl.

Of these compounds, more preferred compounds are those wherein $R^1$ represents hydrogen, the aforesaid $C_1$ to $C_6$ alkyl, a $C_5$ to $C_6$ cycloalkyl, or phenyl, benzyl, phenethyl or phenylpropyl each of which may have at least one halogen; $R^2$ represents the aforesaid $C_1$ to $C_6$ alkyl, and each of Ar represents phenyl, naphthyl, pyridyl, thienyl, pyrrolyl, benzothiazolyl or benzimidazolyl, each of which may be substituted by at least one substituent selected from the group consisting of a $C_1$ to $C_6$ alkyl, a $C_1$ to $C_6$ alkoxy, amino, a halogen, cyano, nitro, a $C_1$ to $C_6$ alkylthio, a $C_6$ to $C_{12}$ arylsulfonyl, aminosulfonyl, trifluoromethyl and imidazolyl.

Specific examples of the preferred compounds of the present invention include, for example, those as shown in the following Table 1.

TABLE 1

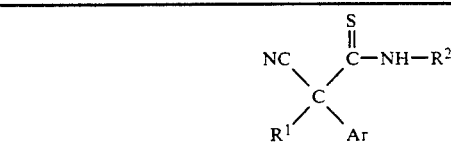

| Compound No. | $R^1$ | $R^2$ | Ar |
|---|---|---|---|
| 1 | —H | —CH$_3$ | -C$_6$H$_4$-Cl |
| 2 | —CH$_3$ | —CH$_3$ | -C$_6$H$_4$-Cl |
| 3 | —C$_2$H$_5$ | —CH$_3$ | -C$_6$H$_4$-Cl |
| 4 | -n-C$_3$H$_7$ | —CH$_3$ | -C$_6$H$_4$-Cl |
| 5 | -isoC$_3$H$_7$ | —CH$_3$ | -C$_6$H$_4$-Cl |
| 6 | -n-C$_4$H$_7$ | —CH$_3$ | -C$_6$H$_4$-Cl |
| 7 | -n-C$_5$H$_{11}$ | —CH$_3$ | -C$_6$H$_4$-Cl |
| 8 | -n-C$_6$H$_{13}$ | —CH$_3$ | -C$_6$H$_4$-Cl |

TABLE 1-continued $$\underset{R^1 \quad Ar}{\overset{NC \quad \overset{S}{\underset{\|}{C}}-NH-R^2}{C}}$$

| Compound No. | R¹ | R² | Ar |
|---|---|---|---|
| 9 | cyclopentyl-CH(H)- | —CH₃ | 4-Cl-C₆H₄— |
| 10 | cyclohexyl-CH(H)- | —CH₃ | 4-Cl-C₆H₄— |
| 11 | —CH₂—C₆H₅ | —CH₃ | 4-Cl-C₆H₄— |
| 12 | —CH₂—C₆H₄—Cl (4-) | —CH₃ | 4-Cl-C₆H₄— |
| 13 | —(CH₂)₂—C₆H₅ | —CH₃ | 4-Cl-C₆H₄— |
| 14 | —(CH₂)₃—C₆H₅ | —CH₃ | 4-Cl-C₆H₄— |
| 15 | —CH₂—(1H-benzimidazol-2-yl) | —CH₃ | 4-Cl-C₆H₄— |
| 16 | —CH₂—(pyridin-3-yl) | —CH₃ | 4-Cl-C₆H₄— |
| 17 | —(CH₂)₂—(pyridin-3-yl) | —CH₃ | 4-Cl-C₆H₄— |
| 18 | —CH₂—(benzothiazol-2-yl) | —CH₃ | 4-Cl-C₆H₄— |
| 19 | —C₆H₅ | —CH₃ | 4-Cl-C₆H₄— |
| 20 | —C₆H₄—Cl (4-) | —CH₃ | 4-Cl-C₆H₄— |

TABLE 1-continued $$\underset{R^1}{\overset{NC}{\diagdown}}\underset{Ar}{\overset{\overset{S}{\|}}{C}}-NH-R^2$$

| Compound No. | R$^1$ | R$^2$ | Ar |
|---|---|---|---|
| 21 | 2-pyridyl | —CH$_3$ | 4-chlorophenyl |
| 22 | 3-thienyl | —CH$_3$ | 4-chlorophenyl |
| 23 | —CH$_3$ | —C$_2$H$_5$ | 4-chlorophenyl |
| 24 | —CH$_3$ | -n-C$_3$H$_7$ | 4-chlorophenyl |
| 25 | —CH$_3$ | -isoC$_3$H$_7$ | 4-chlorophenyl |
| 26 | —CH$_3$ | —C$_4$H$_9$ | 4-chlorophenyl |
| 27 | —CH$_3$ | —C$_5$H$_{11}$ | 4-chlorophenyl |
| 28 | —CH$_3$ | —C$_6$H$_{13}$ | 4-chlorophenyl |
| 29 | —CH$_3$ | —CH$_3$ | phenyl |
| 30 | —CH$_3$ | —CH$_3$ | 2-naphthyl |
| 31 | —CH$_3$ | —CH$_3$ | 2-methylphenyl |

TABLE 1-continued
NC\C(R¹)(Ar)−C(=S)−NH−R²
| Compound No. | R¹ | R² | Ar |
|---|---|---|---|
| 32 | —CH₃ | —CH₃ | 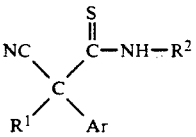 3-CH₃-C₆H₄ |
| 33 | —CH₃ | —CH₃ | 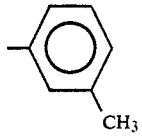 4-CH₃-C₆H₄ |
| 34 | —CH₃ | —CH₃ | 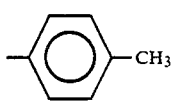 4-C₃H₇-C₆H₄ |
| 35 | —CH₃ | —CH₃ | 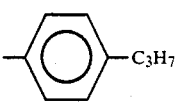 4-t-C₄H₉-C₆H₄ |
| 36 | —CH₃ | —CH₃ | 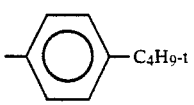 3,5-(CH₃)₂-C₆H₃ |
| 37 | —CH₃ | —CH₃ | 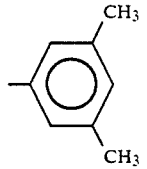 4-OCH₃-C₆H₄ |
| 38 | —CH₃ | —CH₃ | 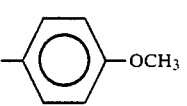 3-OCH₃-C₆H₄ |
| 39 | —CH₃ | —CH₃ | 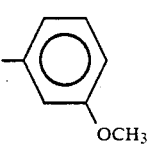 2-OCH₃-C₆H₄ |
| 40 | —CH₃ | —CH₃ | 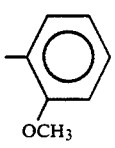 3,4-(OCH₃)₂-C₆H₃ |
| 41 | —CH₃ | —CH₃ | 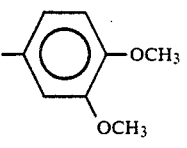 3,5-(OCH₃)₂-4-OH-C₆H₂ |

TABLE 1-continued
$$\underset{R^1}{\overset{NC}{\diagdown}}\underset{Ar}{\overset{\overset{S}{\|}}{C}}\overset{S}{\underset{}{C}}-NH-R^2$$
| Compound No. | R¹ | R² | Ar |
|---|---|---|---|
| 42 | —CH₃ | —CH₃ | 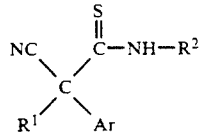 —NH₂ |
| 43 | —CH₃ | —CH₃ | 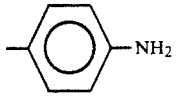 Cl, NH₂ |
| 44 | —CH₃ | —CH₃ | 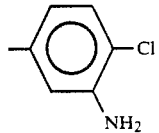 —NHCH₃ |
| 45 | —CH₃ | —CH₃ | 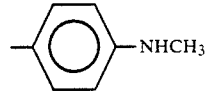 —N(C₂H₅)₂ |
| 46 | —CH₃ | —CH₃ | 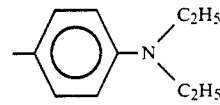 —NHCOCH₃ |
| 47 | —CH₃ | —CH₃ | 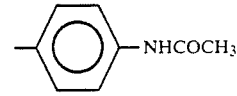 NHCOC₂H₅ |
| 48 | —CH₃ | —CH₃ | 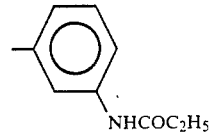 Cl |
| 49 | —CH₃ | —CH₃ | 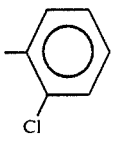 Cl |
| 50 | —CH₃ | —CH₃ | 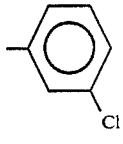 Cl, Cl |
| 51 | —CH₃ | —CH₃ | 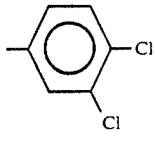 Cl, Cl |

TABLE 1-continued
$$\underset{R^1}{\overset{NC}{\diagdown}}\underset{Ar}{\overset{C}{\diagup}}\overset{\overset{S}{\|}}{C}-NH-R^2$$
| Compound No. | R¹ | R² | Ar |
|---|---|---|---|
| 52 | —CH₃ | —CH₃ | 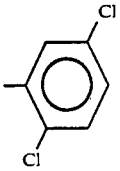 2,5-dichlorophenyl |
| 53 | —CH₃ | —CH₃ | 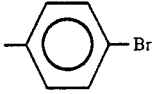 4-bromophenyl |
| 54 | —CH₃ | —CH₃ | 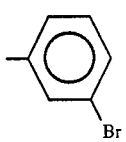 3-bromophenyl |
| 55 | —CH₃ | —CH₃ | 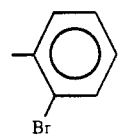 2-bromophenyl |
| 56 | —CH₃ | —CH₃ | 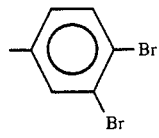 3,4-dibromophenyl |
| 57 | —CH₃ | —CH₃ | 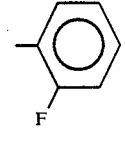 2-fluorophenyl |
| 58 | —CH₃ | —CH₃ | 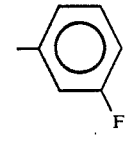 3-fluorophenyl |
| 59 | —CH₃ | —CH₃ | 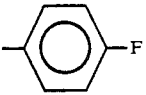 4-fluorophenyl |
| 60 | —CH₃ | —CH₃ | 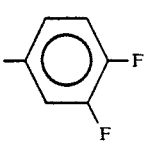 3,4-difluorophenyl |

TABLE 1-continued $$\underset{R^1}{\underset{|}{\overset{NC}{\phantom{|}}}}\underset{Ar}{\overset{\overset{S}{\|}}{C}}-NH-R^2$$

| Compound No. | R¹ | R² | Ar |
|---|---|---|---|
| 61 | —CH₃ | —CH₃ | 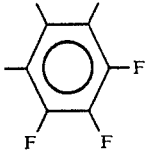 2,3,5,6-tetrafluorophenyl |
| 62 | —CH₃ | —CH₃ | 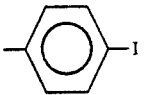 4-iodophenyl |
| 63 | —CH₃ | —CH₃ | 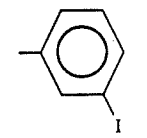 3-iodophenyl |
| 64 | —CH₃ | —CH₃ | 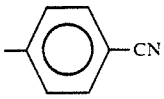 4-cyanophenyl |
| 65 | —CH₃ | —CH₃ | 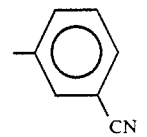 3-cyanophenyl |
| 66 | —CH₃ | —CH₃ | 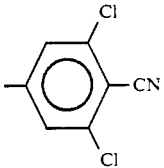 2,6-dichloro-4-cyanophenyl |
| 67 | —CH₃ | —CH₃ | 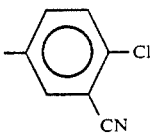 2-chloro-3-cyanophenyl |
| 68 | —CH₃ | —CH₃ | 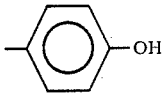 4-hydroxyphenyl |
| 69 | —CH₃ | —CH₃ | 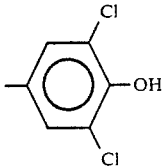 2,6-dichloro-4-hydroxyphenyl |
| 70 | —CH₃ | —CH₃ | 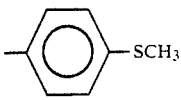 4-methylthiophenyl |

TABLE 1-continued

Structure: NC, C(=S)—NH—R², with central C bearing R¹ and Ar

| Compound No. | R¹ | R² | Ar |
|---|---|---|---|
| 71 | —CH₃ | —CH₃ | 4-(t-C₄H₉S)-C₆H₄— |
| 72 | —CH₃ | —CH₃ | 4-(C₆H₅S)-C₆H₄— |
| 73 | —CH₃ | —CH₃ | 3-(CH₃S)-C₆H₄— |
| 74 | —CH₃ | —CH₃ | 4-(CH₃SO)-C₆H₄— |
| 75 | —CH₃ | —CH₃ | 4-(C₂H₅SO)-C₆H₄— |
| 76 | —CH₃ | —CH₃ | 4-(C₆H₅SO)-C₆H₄— |
| 77 | —CH₃ | —CH₃ | 4-(CH₃SO₂)-C₆H₄— |
| 78 | —CH₃ | —CH₃ | 4-(C₆H₅SO₂)-C₆H₄— |
| 79 | —CH₃ | —CH₃ | 4-(CF₃)-C₆H₄— |
| 80 | —CH₃ | —CH₃ | 3-(CF₃)-C₆H₄— |
| 81 | —CH₃ | —CH₃ | 4-(CH₃CO)-C₆H₄— |

TABLE 1-continued $$\underset{R^1}{\overset{NC}{\diagdown}}\underset{Ar}{\overset{S}{\underset{\|}{C}}}\!\!-\!\!NH\!-\!R^2$$

| Compound No. | R¹ | R² | Ar |
|---|---|---|---|
| 82 | —CH₃ | —CH₃ | —C₆H₄—COC₂H₅ (para) |
| 83 | —CH₃ | —CH₃ | —C₆H₄—COCH₃ (meta) |
| 84 | —CH₃ | —CH₃ | —C₆H₃(OH)(COCH₃) |
| 85 | —CH₃ | —CH₃ | —C₆H₄—CO—C₆H₅ |
| 86 | —CH₃ | —CH₃ | —C₆H₄—NO₂ |
| 87 | —CH₃ | —CH₃ | —C₆H₄—SO₂NH₂ |
| 88 | —CH₃ | —CH₃ | —C₆H₄—SO₂NHCH₃ |
| 89 | —CH₃ | —CH₃ | 4-pyridyl |
| 90 | —CH₃ | —CH₃ | 3-pyridyl |
| 91 | —CH₃ | —CH₃ | 2-pyridyl |
| 92 | —CH₃ | —CH₃ | 3-thienyl |
| 93 | —CH₃ | —CH₃ | 2-thienyl |

TABLE 1-continued
$$\underset{R^1}{\overset{NC}{\diagdown}}\underset{Ar}{\overset{\overset{S}{\|}}{C}}\underset{}{\overset{}{C-NH-R^2}}$$
| Compound No. | R¹ | R² | Ar |
|---|---|---|---|
| 94 | —CH₃ | —CH₃ | 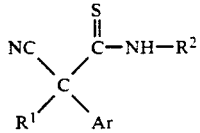 |
| 95 | —CH₃ | —CH₃ | 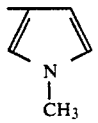 |
| 96 | —CH₃ | —CH₃ | 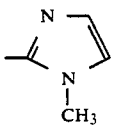 |
| 97 | —CH₃ | —CH₃ | 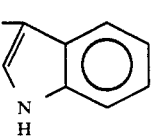 |
| 98 | —CH₃ | —CH₃ | 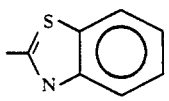 |
| 99 | —CH₃ | —CH₃ | 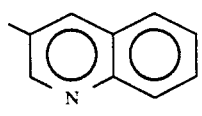 |
| 100 | —CH₃ | —CH₃ | 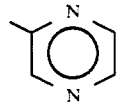 |
| 101 | —CH₃ | —CH₃ | 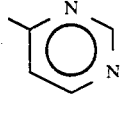 |
| 102 | —CH₃ | —CH₃ | 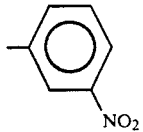 |
| 103 | —CH₃ | —CH₃ | 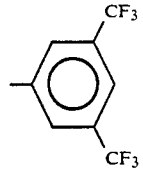 |

TABLE 1-continued $$\underset{R^1}{\overset{NC}{\diagdown}}\underset{Ar}{\overset{\overset{S}{\|}}{C-NH-R^2}}$$

| Compound No. | R¹ | R² | Ar |
|---|---|---|---|
| 104 | —CH₃ | —CH₃ | 2-Cl, 5-SO₂NH₂-phenyl |
| 105 | —CH₃ | —CH₃ | 1-methyl-benzimidazol-5-yl |
| 106 | —CH₃ | —CH₃ | 4-(imidazol-1-yl)phenyl |
| 107 | —C₂H₅ | —CH₃ | 4-(imidazol-1-yl)phenyl |
| 108 | -n-C₃H₇ | —CH₃ | 4-(imidazol-1-yl)phenyl |
| 109 | -iso-C₃H₇ | —CH₃ | 4-(imidazol-1-yl)phenyl |
| 110 | —CH₃ | —C₂H₅ | 4-(imidazol-1-yl)phenyl |
| 111 | —CH₃ | -n-C₃H₇ | 4-(imidazol-1-yl)phenyl |
| 112 | —C₂H₅ | —C₂H₅ | 4-(imidazol-1-yl)phenyl |
| 113 | —CH₃ | —CH₃ | 3-(imidazol-1-yl)phenyl |

TABLE 1-continued $$\underset{R^1}{\overset{NC}{\underset{Ar}{\bigg\backslash}}}C\underset{}{\overset{S}{\underset{\|}{-}}}C-NH-R^2$$

| Compound No. | R¹ | R² | Ar |
|---|---|---|---|
| 114 | —C₂H₅ | —CH₃ | 3-(imidazol-1-yl)phenyl |
| 115 | -n-C₃H₇ | —CH₃ | 3-(imidazol-1-yl)phenyl |
| 116 | -iso-C₃H₇ | —CH₃ | 3-(imidazol-1-yl)phenyl |
| 117 | —CH₃ | —C₂H₅ | 3-(imidazol-1-yl)phenyl |
| 118 | —CH₃ | -n-C₃H₇ | 3-(imidazol-1-yl)phenyl |
| 119 | —C₂H₅ | —C₂H₅ | 3-(imidazol-1-yl)phenyl |
| 120 | —H | —CH₃ | 2-(imidazol-1-yl)-3-cyanophenyl |
| 121 | —CH₃ | —CH₃ | 2-(imidazol-1-yl)-3-cyanophenyl |

TABLE 1-continued $$\underset{R^1}{\underset{|}{\overset{NC}{\diagdown}}}\underset{Ar}{\overset{\overset{\overset{S}{\|}}{C-NH-R^2}}{\diagup}}$$

| Compound No. | R¹ | R² | Ar |
|---|---|---|---|
| 122 | —C₂H₅ | —CH₃ | 2-CN, 6-(imidazol-1-yl)phenyl |
| 123 | —CH₃ | —C₂H₅ | 2-CN, 6-(imidazol-1-yl)phenyl |
| 124 | —H | —CH₃ | 2-CN, 6-(imidazol-1-yl)phenyl |
| 125 | —CH₃ | —CH₃ | 2-CN, 6-(imidazol-1-yl)phenyl |
| 126 | —C₂H₅ | —CH₃ | 2-CN, 6-(imidazol-1-yl)phenyl |

The process for producing the compound of the present invention is as follows.

The compound (I) of the present invention can be produced by, for example, either of the following routes (1) or (2).

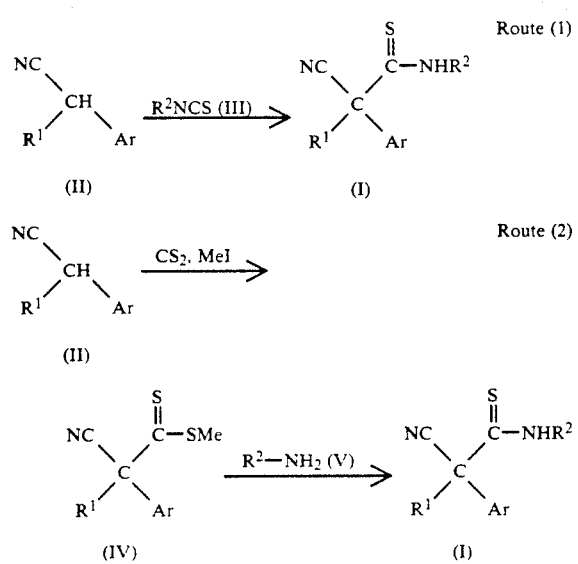

wherein $R^1$, $R^2$ and Ar have the same meanings as defined above.

In the reaction of Route (1), the compound represented by the formula (I) of the present invention can be prepared by reacting the compound represented by the above formula (II) with an isothiocyanate of the formula (III) in an anhydrous polar solvent such as tetrahydrofuran, N,N-dimethylformamide or hexamethylphosphorylamide or a mixture thereof in the presence of a base such as potassium tert-butoxide, lithium diisopropylamide or sodium hydride at $-80°$ C. to $50°$ C.

In the reaction of Route (2), by reacting the compound represented by the formula (II) and carbon disulfide in a polar solvent such as tetrahydrofuran or N,N-dimethylformamide in the presence of a base such as potassium tertbutoxide or sodium hydride at $-80°$ C. to $50°$ C. for several minutes to several hours, and then reacting the resulting solution by adding methyl iodide at $-80°$ C. to $50°$ C., the compound of the above formula (Iv) can be obtained. The compound represented by the above formula (I) of the present invention can be obtained by reacting the compound (IV) and ammonia or the compound represented by the formula $R^2$-$NH_2$ (V) in a polar solvent such as water, methanol, ethanol, N,N-dimethylformamide, tetrahydrofuran or ether, or a mixture thereof, or in an aromatic hydrocarbon such as benzene, toluene or xylene, or in the absence of a solvent at $0°$ C. to $200°$ C.

As for the preparation method of the compound represented by the formula (II), for example, the following Reaction routes (3) to (5) may be employed.

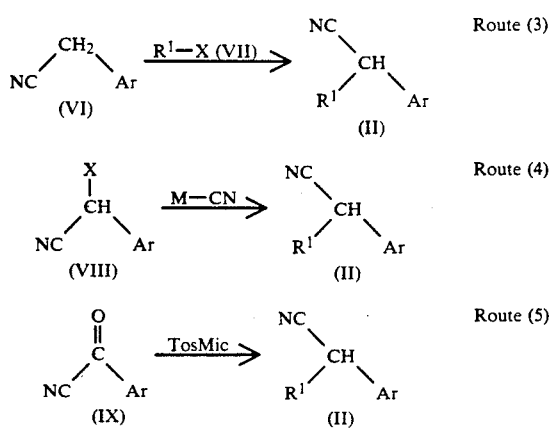

wherein R¹ and Ar have the same meanings as defined above, X represents a halogen atom, an eliminatable group such as —OSO₂CH₃, and M represents an inorganic residue such as metal ion.

In Reaction route (3), the compound represented by the above formula (VI) and the compound represented by the formula (VII) are reacted in a polar solvent such as methanol, ethanol N,N-dimethylformamide, dimethylsulfoxide or tetrahydrofuran in the presence of a base such as sodium hydroxide, sodium ethoxide, potassium tert-butoxide, sodium hydride or lithium diisopropylamide at a temperature of −80° C. to 100° C. to obtain the compound represented by the above formula (II).

In Reaction route (4), the compound represented by the above formula (VIII) and an inorganic cyano compound represented by M-CN are reacted in a polar solvent such as water, methanol, ethanol, acetone, acetonitrile, N,N-dimethylformamide, dimethylsulfoxide or hexamethylphosphorylamide or a mixture thereof, or in a high boiling point solvent such as ethylene glycol and ether thereof or tetrahydrofurfuryl alcohol, or in the absence of a solvent at 0° C. to 200° C. to obtain the compound represented by the above formula (II).

In Reaction route (5), from the compound represented by the above formula (IX) and p-toluenesulfonylmethylisocyanide (TosMic), the compound represented by the above formula (II) can be obtained by the method described in a literature (for example, Oldenziel O. H. and van Leusen A. M., *Tetrahedrom Letters*, No. 16, p. 1357 (1973)).

Further, in the preparation of the compound (I) of the present invention, when Reaction routes (3) and (1) are used, the compound (1) of the present invention can also be obtained from the compound represented by the formula (VI) with one step without isolating the compound represented by the above formula (II) which is an intermediate.

When an asymmetric carbon is present in the compound (I) of the present invention, there exist optical isomer(s), and the compound of the present invention is deamed to include these isomers.

The thiocarbamoylacetonitrile derivative of the present invention exhibits vasodilating activity and hypotensive activity so that it is effective for the treatment of hypertension.

When the compounds according to the present invention are to be used as antihypertensive agents, they can be applied orally or non-orally to a man according to conventional techniques. As a form suitable for oral administration, there may be mentioned granules, fine granules, powders, tablets, hard capsules, soft capsule, syrups, emulsions, suspensions or liquids. Also, as a form suitable for non-oral administration, there may be mentioned injections, suppositories and endermic agents.

The compounds represented by the above formula (I) and pharmaceutically acceptable salts thereof may be contained in the above-described pharmaceutical (or medicinal) agents in combination with pharmacologically acceptable solid or liquid carriers for medicines or additives for medicines conventionally employed, such as excipients, stabilizers, lubricants, edulcorants, preservatives and suspending agents.

Examples of the solid carriers to be used may include lactose, kaolin, sucrose, crystalline cellulose, corn starch, talc, agar, pectin, acacia, stearic acid, magnesium stearate, lecithin and sodium chloride. Examples of the liquid carriers may include syrup, glycerin, peanut oil, polyvinyl pyrrolidone, olive oil, ethanol, benzyl alcohol, propylene glycol and water.

When the compounds of the present invention are to be administered orally, a dose for an adult man is from 0.01 mg to 1000 mg per day, preferably from 0.1 mg to 100 mg per day, which may be preferably and optionally be either increased or decreased depending on the age, sex, condition of the disease, symptoms, and presence or absence of simultaneous treatment. Also, the rate of administration may be either per day or several times per day, with suitable intervals of time between doses.

When a solid pharmaceutical preparation is prepared, as an excipient, for example, lactose, starch, talc, cellulose, dextrin, caolin or calcium carbonate may be used. In the case of a liquid pharmaceutical preparation for oral administration, i.e. syrups, emulsions, suspensions or liquids, the above liquid carriers generally employed are used in combination with a suitable auxiliary agent such as humectants, suspension auxiliary, edulcorants, aromatics, colorants or preservatives.

EXAMPLES

In the following Examples, the present invention is explained in more detail but the invention is not considered to be limited thereby.

Example 1

Synthesis of N-methyl 2-(4 chlorophenyl)-2-cyano-5-phenylthiovaleroamide (Compound No. 14 in Table 1)

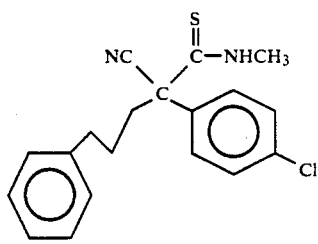

(1) 2 ml of an aqueous sodium hydroxide (1.08 g) solution was added to a 10 ml solution of dimethylsulfoxide containing 1.0 g (6.6 mmole) of 4-chlorophenylacetonitrile and 1.3 g (6.6 mmole) of 1-bromo-3-phenylpropane at room temperature. After stirring for 2 hours under the same conditions, water was added to the reaction mixture and the mixture was extracted with 10 ml of n-hexane, dried, and condensed under reduced pressure to obtain 1.78 g (yield: quantitative) of 2-(4-chlorophenyl)-5-phenylvaleronitrile.

¹H-NMR (CDCl₃): 1.7-2.0 (m, 4H), 2.6-2.7 (m, 2H), 3.7 (dd, 1H), 7.0-7.4 (m, 9H)

(2) To a tetrahydrofuran solution containing 1.78 g (6.6 mmole) of 2-(4-chlorophenyl)-5-phenylvaleronitrile was added a tetrahydrofuran solution containing 0.77 g (6.9 mmole) of potassium tert-butoxide at 0° C. After stirring for 30 minutes, a tetrahydrofuran solution containing 0.5 g (6.8 mmol) of methyl isothiocyanate was added to the mixture and the mixture was stirred at room temperature for 2 hours. Water was added to the reaction mixture, and the mixture was extracted with ethyl acetate, dried and condensed under reduced pressure, and then purified by silica gel chromatography to obtain 1.19 g (yield: 52.4 %) of N-methyl-2-(4-chlorophenyl)-2-cyano-5-phenylthiovaleroamide as a crystal.

¹H-NMR (CDCl₃): 1.65 (m, 1H), 1 82 (m, 1H), 2.35 (tt, 1H), 2.70 (m, 3H), 3.14 (d, 3H), 7.1-7.5 (m, 9H), 7.9 (brs , 1H)

IR₁: 3380, 2230, 1640, 1530 cm⁻¹ Melting point: 125.5°-126° C.

EXAMPLE 2

Synthesis of N-methyl-2-(4-chlorophenyl)-2-cyanothiopropionamide (Compound No. 2 in Table 1)

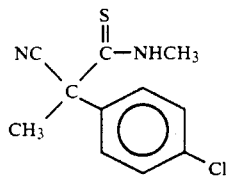

(1) To a 100 ml N,N-dimethylformamide suspension containing 4.0 g (0.10 mole) of 60 % oily sodium hydride was added a 200 ml N,N-dimethylformamide solution containing 15.2 g (0.10 mole) of 4-chlorophenylbenzylcyanide under ice-cooling. Stirring was continued for 0.5 hour under the same conditions, and then a 20 ml N,N-dimethylformamide solution containing 6.2 ml (0 10 mole) of methyl iodide was added to the mixture and the mixture was stirred for further 2 hours. The solvent was removed from the reaction mixture under reduced pressure, water was added to the residue and the mixture was extracted with 150 ml of dichloromethane, dried and condensed, and then purified by silica gel column chromatography to obtain 7 8 g (yield: 47.1 %) of 4-chlorophenylmethylbenzylcyanide.

¹H-NMR (CDCl₃): 1.6 (d, 3H), 3.8-3.9 (dd, 1H), 7.2-7.3 (dd, 4H)

(2) To a 10 ml tetrahydrofuran solution containing 1.00 g (6 mmole) of 4-chlorophenylmethylbenzylcyanide was added a 3.2 ml tetrahydrofuran solution containing 2 M of lithium diisopropylamide at −60° C. After stirring for 30 minutes under the same conditions, a 5 ml tetrahydrofuran solution containing 0.44 g (6 mmol) of methyl isothiocyanate was added to the mixture and the mixture was allowed to stand at room temperature overnight. The solvent was removed from the reaction mixture under reduced pressure and water was added to the residue. The mixture was extracted with 50 ml of ethyl acetate, dried and condensed under reduced pressure, and then purified by silica gel chromatography and recrystallized from hexane to obtain 0.45 g (yield: 31.4 %) of N-methyl-2-(4-chlorophenyl)-2-cyano-thiopropionamide.

¹H-NMR (CDCl₃) ppm: 2.1 (s, 3H), 3.1 (d, 3H), 7.3-7.5 (dd, 4H), 7.9 (brs., 1H)

IR (KBr): 3325, 2250, 1645, 1540 cm⁻¹ Melting point: 91.5° C.

EXAMPLE 3

Synthesis of N-methyl-2-(1,3-benzothiazol-2-yl)-2-cyanothiopropionamide (Compound No. 97 in Table 1)

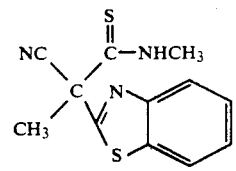

To a tetrahydrofuran solution containing 1.74 g (10 mmole) of 2-cyanomethyl-1,3-benzothiazole was added a tetrahydrofuran solution containing 1.42 g (10 mmol) of methyl iodide at −70° C. in the presence of 1.12 g (10 mmole) of potassium tert-butoxide. After the addition, the temperature was gradually raised to 0° C. and the mixture was stirred at the same temperature for one hour. Then, 1.35 g (12 mmole) of potassium tert-butoxide was added to the mixture and the mixture was further stirred for one hour; 0.88 g (12 mmole) of methyl isothiocyanate was then added and the mixture was stirred at room temperature overnight.

After addition of water, the mixture was extracted with ethyl acetate, dried and condensed under reduced pressure, and then purified by silica gel chromatography to obtain 0.59 g (yield 22.6%) of N-methyl-2-(1,3-benzothiazol-2-yl)-2-cyano-thiopropionamide as a crystalline solid.

Melting point: 159°-161° C.

¹H-NMR (CDCl₃) ppm: 2.3 (s, 3H), 3.2 (d, 3H), 7.4-7.6 (m, 2H), 7.9 (dd, 1H), 8.1 (dd, 1H), 9.1 (brs., 1H)

IR (KBr): 3250, 2250, 1640, 1540 cm⁻¹

EXAMPLE 4

Synthesis of N-methyl-2-(4-cyanophenyl)-2-cyano-thiopropionaimde (Compound No. 64 in Table 1)

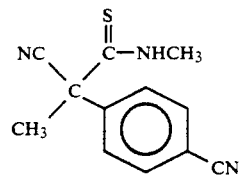

(1) 1.40 g (1.25 mmole) of potassium tert-butoxide was added to a 17 ml ethylene glycol dimethyl ether solution containing 0.73 g (5 mmole) of 4-acetylbenzonitrile, 0.5 ml of ethanol and 1.27 g (6.5 mmole) of p-toluenesulfonylmethylisocyanide under ice-cooling; then the mixture was stirred at room temperature for 0.5 hour and then at 40° C. for an additional hour. After the reaction mixture was cooled by allowing to stand at room temperature, it was filtered under reduced pressure and the filtrate was purified by silica gel chromatography to obtain 0.55 g (yield: 70.4 %) of 2-(4-cyanophenyl)ethylcyanide.

$^1$H-NMR (CDCl$_3$) ppm: 1.6 (d, 3H), 3.9–4.0 (dd, 1H), 7.4–7.7 (dd, 4H)

IR (neat): 2330 cm$^{-1}$ (2) To a 10 ml tetrahydrofuran solution containing 0.53 g (3.3 mmole) of 2-(4-cyanophenyl)ethylcyanide was added a 5 ml tetrahydrofuran solution containing 0.38 g (3.3 mmole) of potassium tert-butoxide under ice-cooling. The mixture was stirred under the same conditions for 0.5 hour, then a 2 ml tetrahydrofuran solution containing 0.26 g (3.5 mmole) of methyl isothiocyanate was added thereto and the mixture was stirred under the same conditions for another 2 hours. Water was added to the reaction mixture and the mixture was extracted with 20 ml of ethyl acetate, dried and condensed. The residue was then purified by silica gel chromatography and further recrystallized from hexane to obtain 0.40 g (yield: 52.9 %) of N-methyl 2-(4-cyanophenyl)-2-cyanothiopropinonamide.

$^1$H-NMR (CDCl$_3$) ppm: 2.1 (s, 3H), 3.1–3.2 (d, 3H), 7.7 (s, 4H), 7.9 (brs., 1H)

IR (KBr): 3295, 2440, 1640, 1535 cm$^{-1}$ Melting point: 135.5°–136° C.

EXAMPLE 5

Synthesis of N-methyl-2-[4-(1-imidazolyl)-phenyl]-2-cyanothiopropionamide (Compound No. 106 in Table 1)

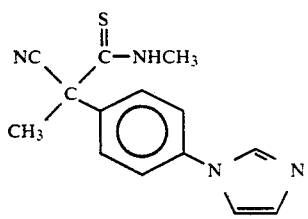

(1) To a 25 ml ethylene glycol solution containing 1.86 g (10 mmole) of 4-(1-imidazolyl)-acetophenone, 1 ml of ethanol and 3.00 g (15.4 mmole) of p-toluenesulfonylmethyl isocyanide was added 1.70 g (15.1 mmole) of potassium tertbutoxide under ice-cooling, and the mixture was stirred at room temperature for 0.5 hour and further at 40° C. for 2 hours. After the reaction mixture was cooled by allowing it to stand, water was added and the mixture was extracted with 25 ml of ethyl acetate, dried and condensed, and then purified by silica gel chromatography to obtain 1.02 g (yield: 52 %) of 2-[4-(1-imidazolyl)-phenyl]propionitrile as an oily product.

$^1$H-NMR (CDCl$_3$) ppm: 1.69 (d, 3H), 3.98 (dd, 1H), 7.22 (s, 1H), 7.27 (s, 1H), 7.41–7.51 (m, 4H), 7.86 (s, 1H)

IR (KBr): 2250 cm$^{-1}$ (2) To a 10 ml tetrahydrofuran solution containing 1.00 g (5.1 mmole) of 2-[4-(1-imidazolyl)-phenyl]propionitrile was added a 10 ml tetrahydrofuran solution containing 0.69 g (6.2 mmole) of potassium tert-butoxide at 0 C. After stirring for 0.5 hour, a 5 ml tetrahydrofuran solution containing 0.45 g (6.2 mmole) of methyl isothiocyanate was added to the mixture and the mixture was stirred at room temperature for 2 hours. Water was added to the mixture and the mixture was extracted with 20 ml of ethyl acetate, dried and condensed under reduced pressure, and then purified by silica gel chromatography and condensed. The resulting condensate was suspended in 30 ml of toluene and the suspension was refluxed under heating for 0.5 hour and a solid was collected by filtration to obtain 0.75 g (yield: 54 %) of N-methyl-2-[4-(1-imidazolyl)-phenyl]-2cyanothiopropionamide as a crystalline solid.

$^1$H-NMR (CDCl$_3$) ppm: 2.18 (s, 3H), 3.21 (d, 3H), 7.21 (s, 1H), 7.28 (s, 1H), 7.41 (d, 2H), 7.68 (d, 2H), 7.80 (s, 1H), 8.20 (brs., 1H)

IR (KBr): 3250, 2250, 1640 cm$^{-1}$ Melting point: 183°–184.5° C.

EXAMPLE 6

According to the procedure provided above in Examples 1 to 5, the compounds listed in Table 2 were likewise prepared (Compound No. corresponds to that shown in Table 1).

TABLE 2

| Compound No. | Melting point (°C.) |
|---|---|
| 1 | 101.5–102.5 |
| 3 | 88–88.5 |
| 4 | 106.5 |
| 8 | 86 |
| 10 | 163–163.5 |
| 11 | 142 |
| 20 | 152.2–153 |
| 23 | 68 |
| 24 | 64–64.5 |
| 25 | 90–90.5 |
| 29 | 116.5 |
| 30 | 145–146 |
| 31 | 159 |
| 32 | 105 |
| 33 | 131–132.5 |
| 37 | 65.5–66 |
| 39 | 160.5–161.5 |
| 43 | 154.5–155 |
| 48 | 175.5–176.5 |
| 49 | 115.5 |
| 50 | 163–164.5 |
| 51 | 105–105.5 |
| 53 | 104.5–105 |
| 59 | 83 |
| 60 | 77 |
| 65 | 135–139 |
| 70 | 109.5 |
| 78 | 145–146 |
| 79 | 102–102.5 |
| 80 | oil |
| 86 | 120–121.5 |
| 89 | 133.5–134.5 |
| 92 | 135–135.5 |
| 93 | 112 |
| 94 | 126–128 |
| 101 | 113–114 |
| 102 | oil |
| 104 | 162–163.5 |
| 105 | 138.5 |
| 113 | 167.5 |

TEST EXAMPLE

To demonstrate the antihypertensive activity of the compounds of the present invention, hypertension spontaneously occurred rats (OKAMOTO-AOKI series, showing an average blood pressure of 150 mmHg or higher, were administered 10 mg/kg of the compound of the present invention, and then the rat blood pressure and heart rate were measured by the direct method described in Nakao K., H and Takayanagi K., *Japanese Journal of Pharmacology*, Vol. 25, p. 25 (1975).

The results 2 hours after the administration of the compounds, are shown in Table 3 below.

TABLE 3

| Compound No. | Average blood pressure (mm Hg) | | Heart rate (bpm) | |
| --- | --- | --- | --- | --- |
| | Before administration | Decrease in blood pressure | Before administration | Increase in heart rate |
| 1 | 171.3 | 21.4 | 301.4 | 68.8 |
| 29 | 181.9 | 14.5 | 266.5 | 13.0 |
| 59 | 184.2 | 17.3 | 298.5 | 10.0 |
| 60 | 179.1 | 23.7 | 324.0 | 39.3 |
| 65 | 170.0 | 33.2 | 304.5 | 51.3 |
| 80 | 180.3 | 17.3 | 296.5 | 15.5 |
| 86 | 160.4 | 32.2 | 272.0 | 26.5 |
| 101 | 171.8 | 27.4 | 281.0 | 10.0 |
| 102 | 172.5 | 19.7 | 292.0 | 13.5 |
| 104 | 182.1 | 22.2 | 314.5 | −2.5 |
| 106 | 173.4 | 97.8 | 281.0 | 146.5 |
| 113 | 173.3 | 88.3 | 281.0 | 118.5 |

The compounds of the present invention clearly show good hypotensive activity, demonstrating that they can be effectively used as an antihypertensive agents.

What is claimed is:

1. A thiocarbamoylacetonitrile compound represented by the formula (1):

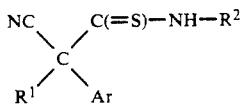

wherein $R^1$ is selected from the group consisting of hydrogen, a $C_1$ to $C_6$ alkyl, a $C_3$ to $C_6$ cycloalkyl or —$(CH_2)_n$—A and where A is selected from the group consisting of a $C_6$ to $C_{12}$ aryl, each of which may be substituted by at least one substituent group selected from a $C_1$ to $C_6$ alkyl and a halogen and n is 0 or an integer of 1 to 6 and $R^2$ represents a $C_1$ to $C_{10}$ alkyl, and Ar represents imidazole-phenyl each of which may be substituted by at least one substituent group selected from the group consisting of $C_1$ to $C_6$ alkyl, a $C_1$ to $C_6$ alkoxy, a $C_2$ to $C_7$ alkylcarbonyl, a C2 to $C_6$ dialkylamino, amino, formylamino, a $C_2$ to $C_7$ alkylcarbonylamino, a halogen, cyano, nitro, hydroxyl, a $C_1$ to $C_6$ alkylthio, a $C_6$ to $C_{12}$ arylsulfinyl, a $C_1$ to $C_6$ a alkylsulfinyl, a $C_6$ to $C_{12}$ alkylsulfonyl, a $C_6$ to $C_{12}$ arylsulfonyl, aminosulfonyl, a $C_1$ to $C_6$ alkylaminosulfonyl, a $C_2$ to $C_6$ dialkylaminosulfonyl, trifluoromethyl.

2. The compound according to claim 1, wherein $R^2$ is a $C_1$ to $C_6$ alkyl group.

3. The compound according to claim 2, wherein $R^1$ is selected from the group consisting of hydrogen, a $C^1$ to $C_6$ alkyl, a $C_4$ to $C_6$ cycloalkyl or —$(CH_2)_n$—A (where A represents phenyl, pyridyl, thienyl, benzimidazolyl or benzothiazolyl, each of which may be substituted by at least one substituent selected from the group consisting of a $C_1$ to $C_3$ alkyl and a halogen, and n is 0 or an integer of 1 to 3).

4. The compound according to claim 3, wherein Ar is selected from the group consisting of phenyl, naphthyl, pyridyl, thienyl, pyrrolyl, imidazolyl, pyrazinyl, pyrimidinyl, indolyl, benzothiazolyl, benzimidazolyl or quinolyl, each of which may be substituted by at least one substituent selected from the group consisting of a $C_1$ to $C_6$ alkyl, a $C_1$ to $C_6$ alkoxy, a $C_2$ to $C_7$ alkylcarbonyl, a $C_7$ to $C_{13}$ arylcarbonyl, a $C_1$ to $C_6$ alkylamino, a $C_2$ to $C_6$ dialkylamino, amino, formylamino, a $C_2$ to $C_7$ alkylcarbonylamino, a halogen, cyano, nitro, hydroxyl, a $C_1$ to $C_6$ alkylthio, a $C_6$ to $C_{12}$ arylthio, a $C_1$ to $C_6$ alkylsulfinyl, a $C_6$ to $C_{12}$ arylsulfinyl, a $C_1$ to $C_6$ alkylsulfonyl, a $C_6$ to $C_{12}$ arylsulfonyl, aminosulfonyl, a $C_1$ to $C_6$ alkylaminosulfonyl, a $C_2$ to $C_6$ dialkylaminosulfonyl, trifluoromethyl and imidazolyl.

5. The compound according to claim 4, wherein $R^1$ is selected from the group consisting of hydrogen, a $C_1$ to $C_6$ alkyl, a $C_5$ to $C_6$ cycloalkyl, or phenyl, benzyl, phenethyl or phenylpropyl, each of which may have at least one halogen atom as a substituent.

6. The compound according to claim 5, wherein Ar is selected from the group consisting of phenyl, naphthyl, pyridyl, thienyl, pyrrolyl, benzothiazolyl or benzimidazolyl, each of which may be substituted by at least one substituent selected from the group consisting of a $C_1$ to $C_6$ alkyl, a $C_1$ to $C_6$ alkoxy, amino, a halogen, cyano, nitro, a $C_1$ to $C_6$ alkylthio, a $C_6$ to $C_{12}$ arylsulfonyl, aminosulfonyl, trifluoromethyl and imidazolyl.

7. A pharmaceutical composition useful in treating hypertension in mammals comprising an effective antihypertensive amount of at least one of the compounds of claim 1, and a pharmaceutically acceptable carrier.

8. A method of treating hypertension in mammals which comprises administering thereto an effective amount of the pharmaceutical composition according to claim 7.

* * * * *